United States Patent
Radtkey et al.

(10) Patent No.: US 8,993,346 B2
(45) Date of Patent: Mar. 31, 2015

(54) MAGNETIC CARBON NANOTUBE BASED BIODETECTION

(75) Inventors: Ray Radtkey, Oakland, CA (US); Kanchan Joshi, Emeryville, CA (US); Bradley N. Johnson, Berkeley, CA (US); Ying-Lan Chang, Cupertino, CA (US)

(73) Assignee: Nanomix, Inc., Emeryville, CA (US)

( * ) Notice: Subject to any disclaimer, the term of this patent is extended or adjusted under 35 U.S.C. 154(b) by 0 days.

(21) Appl. No.: 13/389,247

(22) PCT Filed: Aug. 6, 2010

(86) PCT No.: PCT/US2010/044778
§ 371 (c)(1),
(2), (4) Date: Mar. 27, 2012

(87) PCT Pub. No.: WO2011/017660
PCT Pub. Date: Feb. 10, 2011

(65) Prior Publication Data
US 2012/0178187 A1 Jul. 12, 2012

Related U.S. Application Data

(60) Provisional application No. 61/232,242, filed on Aug. 7, 2009.

(51) Int. Cl.
*G01N 33/563* (2006.01)
*G01N 33/553* (2006.01)
(Continued)

(52) U.S. Cl.
CPC ............ *G01N 33/5438* (2013.01); *B82Y 15/00* (2013.01); *B82Y 30/00* (2013.01);
(Continued)

(58) Field of Classification Search
None
See application file for complete search history.

(56) References Cited

U.S. PATENT DOCUMENTS

| 3,860,430 A | 1/1975 | Walker et al. |
| 4,022,059 A | 5/1977 | Schontzler et al. |

(Continued)

FOREIGN PATENT DOCUMENTS

| CN | 1546365 A | 11/2004 |
| CN | 101035620 A | 9/2007 |

(Continued)

OTHER PUBLICATIONS

Cai, D. et al., "Highly efficient molecular delivery into mammalian cells using carbon nanotube spearing", Nature Methods (2005), 2(6):449-454.*

(Continued)

*Primary Examiner* — Bao Thuy L Nguyen
*Assistant Examiner* — Gary E Hollinden
(74) *Attorney, Agent, or Firm* — Weaver Austin Villeneuve & Sampson LLP (57) ABSTRACT

Provided herein is a new hybrid material system, mCNT, including magnetic carbon nanotubes for biological and medical sensing applications. In certain embodiments, the systems include magnetic material on the interior of carbon nanotubes (CNTs). The amount of magnetic particles inside CNTs may be such that mCNT can respond to small, low cost, portable magnet. The exterior CNT surface is kept intact for biomolecular attachments or other functionalizations. Performance enhancement with this novel material includes improved sensitivity, reduced response time, and reduced sample volume. According to various embodiments, the mCNTs are substrates for the adherence of molecules participating in these assays or as active sensing elements. Also provided are methods of fabricating two-dimensional mCNT and CNT networks on printed electrodes.

7 Claims, 5 Drawing Sheets

(51) Int. Cl.

| | | |
|---|---|---|
| G01N 33/543 | (2006.01) | |
| B82Y 15/00 | (2011.01) | |
| B82Y 30/00 | (2011.01) | |
| B82Y 40/00 | (2011.01) | |
| C01B 31/02 | (2006.01) | |
| G01N 27/22 | (2006.01) | |

(52) U.S. Cl.
CPC ............ *B82Y 40/00* (2013.01); *C01B 31/0226* (2013.01); *C01B 31/0233* (2013.01); *C01B 31/0273* (2013.01); *G01N 27/226* (2013.01)
USPC ............................. 436/512; 436/513; 436/526

(56) References Cited

U.S. PATENT DOCUMENTS

| | | | |
|---|---|---|---|
| 4,467,032 A | 8/1984 | Lowke et al. | |
| 4,795,968 A | 1/1989 | Madou et al. | |
| 4,851,195 A | 7/1989 | Matthews et al. | |
| 4,909,919 A | 3/1990 | Morris et al. | |
| 4,935,345 A | 6/1990 | Guilbeau et al. | |
| 4,945,045 A * | 7/1990 | Forrest et al. ................... | 435/25 |
| 5,246,859 A | 9/1993 | Nelson et al. | |
| 5,258,415 A | 11/1993 | Hahn et al. | |
| 5,382,417 A | 1/1995 | Haase | |
| 5,448,905 A | 9/1995 | Stetter et al. | |
| 5,618,496 A | 4/1997 | Hasumi et al. | |
| 5,674,752 A | 10/1997 | Buckley et al. | |
| 5,759,773 A | 6/1998 | Tyagi et al. | |
| 5,827,997 A | 10/1998 | Chung et al. | |
| 5,866,434 A * | 2/1999 | Massey et al. ................. | 436/526 |
| 5,958,340 A | 9/1999 | Meyer et al. | |
| 5,993,694 A | 11/1999 | Ito et al. | |
| 6,004,494 A | 12/1999 | Debe et al. | |
| 6,010,459 A | 1/2000 | Silkoff et al. | |
| 6,031,454 A | 2/2000 | Lovejoy et al. | |
| 6,033,916 A | 3/2000 | Sieben et al. | |
| 6,044,843 A | 4/2000 | O'Neil et al. | |
| 6,090,545 A | 7/2000 | Wohlstadter et al. | |
| 6,111,280 A | 8/2000 | Gardner et al. | |
| 6,217,828 B1 | 4/2001 | Bretscher et al. | |
| 6,286,226 B1 | 9/2001 | Jin | |
| 6,287,874 B1 | 9/2001 | Hefti | |
| 6,320,295 B1 | 11/2001 | McGill et al. | |
| 6,346,189 B1 | 2/2002 | Dai et al. | |
| 6,445,006 B1 | 9/2002 | Brandes et al. | |
| 6,465,132 B1 | 10/2002 | Jin | |
| 6,482,639 B2 | 11/2002 | Snow et al. | |
| 6,485,905 B2 | 11/2002 | Hefti | |
| 6,489,394 B1 | 12/2002 | Andros | |
| 6,528,020 B1 * | 3/2003 | Dai et al. ........................ | 422/98 |
| 6,577,242 B2 | 6/2003 | Jen et al. | |
| 6,628,053 B1 | 9/2003 | Den et al. | |
| 6,656,712 B1 * | 12/2003 | Balavoine et al. ............. | 435/176 |
| 6,676,904 B1 | 1/2004 | Lee et al. | |
| 6,797,325 B2 | 9/2004 | Wang et al. | |
| 6,890,780 B2 | 5/2005 | Lee | |
| 6,894,359 B2 | 5/2005 | Bradley et al. | |
| 7,013,708 B1 | 3/2006 | Cho et al. | |
| 7,015,046 B2 * | 3/2006 | Wohlstadter et al. .......... | 436/172 |
| 7,109,859 B2 | 9/2006 | Peeters | |
| 7,262,991 B2 | 8/2007 | Zhang et al. | |
| 7,271,720 B2 | 9/2007 | Tabe | |
| 7,312,095 B1 | 12/2007 | Gabriel et al. | |
| 7,449,757 B2 | 11/2008 | Bradley et al. | |
| 7,473,651 B2 | 1/2009 | Moriya et al. | |
| 7,522,040 B2 | 4/2009 | Passmore et al. | |
| 7,547,931 B2 | 6/2009 | Star et al. | |
| 7,948,041 B2 | 5/2011 | Bryant et al. | |
| 8,154,093 B2 | 4/2012 | Bradley et al. | |
| 8,754,454 B2 | 6/2014 | Bryant et al. | |
| 2002/0012937 A1 | 1/2002 | Tender et al. | |
| 2002/0014667 A1 | 2/2002 | Shin et al. | |
| 2002/0017300 A1 | 2/2002 | Hickle et al. | |
| 2002/0092779 A1 | 7/2002 | Essalik et al. | |
| 2002/0117659 A1 | 8/2002 | Lieber et al. | |
| 2002/0118027 A1 | 8/2002 | Routkevitch et al. | |
| 2002/0127733 A1 | 9/2002 | Kovacs | |
| 2002/0130333 A1 | 9/2002 | Watanabe et al. | |
| 2002/0172639 A1 | 11/2002 | Horiuchi et al. | |
| 2002/0172963 A1 * | 11/2002 | Kelley et al. ..................... | 435/6 |
| 2003/0031620 A1 * | 2/2003 | Harutyunyan et al. ....... | 423/461 |
| 2003/0036065 A1 | 2/2003 | Gellibolian | |
| 2003/0041438 A1 | 3/2003 | Wei et al. | |
| 2003/0073919 A1 | 4/2003 | Hampton et al. | |
| 2003/0113713 A1 | 6/2003 | Glezer et al. | |
| 2003/0134267 A1 | 7/2003 | Kang et al. | |
| 2003/0134433 A1 | 7/2003 | Gabriel et al. | |
| 2003/0139003 A1 | 7/2003 | Gole et al. | |
| 2003/0171257 A1 | 9/2003 | Stirbl et al. | |
| 2003/0175161 A1 | 9/2003 | Gabriel et al. | |
| 2003/0180640 A1 | 9/2003 | Darty | |
| 2003/0199172 A1 | 10/2003 | Rueckes et al. | |
| 2003/0211637 A1 | 11/2003 | Schoeniger et al. | |
| 2004/0011291 A1 | 1/2004 | Delaunay et al. | |
| 2004/0018587 A1 | 1/2004 | Makowski et al. | |
| 2004/0023428 A1 | 2/2004 | Gole et al. | |
| 2004/0029297 A1 | 2/2004 | Bonnell et al. | |
| 2004/0033525 A1 | 2/2004 | Monforte et al. | |
| 2004/0043527 A1 | 3/2004 | Bradley et al. | |
| 2004/0065970 A1 | 4/2004 | Blanchet-Fincher | |
| 2004/0067530 A1 | 4/2004 | Gruner | |
| 2004/0091285 A1 | 5/2004 | Lewis | |
| 2004/0104129 A1 | 6/2004 | Gu et al. | |
| 2004/0119141 A1 | 6/2004 | Schreiter et al. | |
| 2004/0120183 A1 | 6/2004 | Appenzeller et al. | |
| 2004/0132070 A1 | 7/2004 | Star et al. | |
| 2004/0136866 A1 | 7/2004 | Pontis et al. | |
| 2004/0158410 A1 | 8/2004 | Ono et al. | |
| 2004/0188780 A1 | 9/2004 | Kurtz | |
| 2004/0192072 A1 | 9/2004 | Snow et al. | |
| 2004/0200734 A1 | 10/2004 | Co et al. | |
| 2004/0202603 A1 | 10/2004 | Fischer et al. | |
| 2004/0204915 A1 | 10/2004 | Steinthal et al. | |
| 2004/0211580 A1 | 10/2004 | Wang et al. | |
| 2004/0214176 A1 | 10/2004 | Osborne et al. | |
| 2004/0219090 A1 | 11/2004 | Dziedzic et al. | |
| 2005/0003355 A1 | 1/2005 | Lu et al. | |
| 2005/0065741 A1 | 3/2005 | Segal et al. | |
| 2005/0072213 A1 | 4/2005 | Besnard et al. | |
| 2005/0103097 A1 | 5/2005 | Faltum et al. | |
| 2005/0112052 A1 | 5/2005 | Gu et al. | |
| 2005/0129573 A1 | 6/2005 | Gabriel et al. | |
| 2005/0157445 A1 | 7/2005 | Bradley et al. | |
| 2005/0211572 A1 | 9/2005 | Buck et al. | |
| 2005/0245836 A1 | 11/2005 | Star et al. | |
| 2005/0255313 A1 * | 11/2005 | Kyotani et al. ................ | 428/338 |
| 2005/0279987 A1 | 12/2005 | Star et al. | |
| 2006/0009707 A1 | 1/2006 | Daniels et al. | |
| 2006/0009797 A1 | 1/2006 | Armstrong | |
| 2006/0014172 A1 | 1/2006 | Muller et al. | |
| 2006/0035215 A9 | 2/2006 | Sorge et al. | |
| 2006/0040294 A1 | 2/2006 | Prudent et al. | |
| 2006/0054936 A1 | 3/2006 | Lieber et al. | |
| 2006/0055392 A1 | 3/2006 | Passmore et al. | |
| 2006/0102494 A1 | 5/2006 | Chueh et al. | |
| 2006/0228723 A1 | 10/2006 | Bradley et al. | |
| 2006/0232278 A1 | 10/2006 | Diamond et al. | |
| 2006/0249402 A1 | 11/2006 | Snow et al. | |
| 2006/0263255 A1 | 11/2006 | Han et al. | |
| 2007/0048181 A1 | 3/2007 | Chang et al. | |
| 2007/0114138 A1 | 5/2007 | Krasteva et al. | |
| 2007/0114573 A1 | 5/2007 | Han et al. | |
| 2007/0132043 A1 | 6/2007 | Bradley et al. | |
| 2007/0158642 A1 | 7/2007 | Gruner | |
| 2007/0178477 A1 | 8/2007 | Joiner et al. | |
| 2007/0208243 A1 | 9/2007 | Gabriel et al. | |
| 2007/0259359 A1 | 11/2007 | Briman et al. | |
| 2007/0281156 A1 | 12/2007 | Lieber et al. | |
| 2008/0021339 A1 | 1/2008 | Gabriel et al. | |
| 2008/0093226 A1 | 4/2008 | Briman et al. | |
| 2008/0159960 A1 * | 7/2008 | Klingeler et al. ............. | 424/9.32 |
| 2008/0221806 A1 | 9/2008 | Bryant et al. | |
| 2009/0101996 A1 | 4/2009 | Bradley et al. | |

(56) References Cited

U.S. PATENT DOCUMENTS

| | | | |
|---|---|---|---|
| 2009/0165533 A1 | 7/2009 | Han | |
| 2010/0047901 A1 | 2/2010 | Bradley et al. | |
| 2010/0085067 A1 | 4/2010 | Gabriel et al. | |
| 2010/0137731 A1 | 6/2010 | Star et al. | |
| 2012/0006102 A1 | 1/2012 | Bryant et al. | |
| 2012/0052004 A1* | 3/2012 | Wilson et al. | 424/1.11 |
| 2013/0075794 A1 | 3/2013 | Bradley et al. | |

FOREIGN PATENT DOCUMENTS

| | | | |
|---|---|---|---|
| EP | 1 645 871 | 4/2006 | |
| EP | 1 664 724 | 6/2006 | |
| EP | 1 680 353 | 7/2006 | |
| EP | 1 941 270 | 7/2008 | |
| JP | 2002-503204 | 1/2002 | |
| JP | 2003-517604 | 5/2003 | |
| JP | 2005-507121 | 3/2005 | |
| KR | 10-2004-0080184 A | 9/2004 | |
| KR | 2006/0100811 A * | 10/2005 | |
| KR | 10-2007-0089236 A | 8/2007 | |
| WO | WO 97/32571 | 9/1997 | |
| WO | WO 01/32951 | 5/2001 | |
| WO | WO 01/44796 | 6/2001 | |
| WO | WO 02/15240 | 2/2002 | |
| WO | WO 02/48701 | 6/2002 | |
| WO | WO 02/079514 | 10/2002 | |
| WO | WO 02/095099 | 11/2002 | |
| WO | WO 03/016901 | 2/2003 | |
| WO | WO 03/046536 | 6/2003 | |
| WO | WO 2004/044586 | 5/2004 | |
| WO | WO 2005/026694 | 3/2005 | |
| WO | WO 2005/047468 | 5/2005 | |
| WO | WO 2005/062031 | 7/2005 | |
| WO | WO 2005/094221 | 10/2005 | |
| WO | WO 2005/097672 | 10/2005 | |
| WO | WO 2006/024023 | 3/2006 | |
| WO | WO 2006/068250 A1 * | 6/2006 | C07K 14/195 |
| WO | WO 2006/071895 | 7/2006 | |
| WO | WO 2007/114931 | 10/2007 | |
| WO | WO 2008/039165 | 4/2008 | |
| WO | WO 2008/052104 | 5/2008 | |
| WO | WO 2011/017660 | 2/2011 | |
| WO | WO 2011/017660 A3 * | 2/2011 | B82B 3/00 |

OTHER PUBLICATIONS

Lin, Y. et al., "Carbon nanotubes for immunomagnetic separation of *Escherichia coli* O157:H7", J. Nanosci. Nanotechnol. (2006), 6(3):868-871.*

Hu, P. et al., "Magnetic particle-based sandwich sensor with DNA-modified carbon nanotubes as recognition elements for detection of DNA hybridization", Analytical Chemistry (2008), 80(5):1819-1823.*

Soldano, C. et al., "Detection of nanoscale magnetic activity using a single carbon nanotube", Nano Letters (2008), 8(12):4498-4505.*

U.S. Appl. No. 12/960,200, filed Dec. 3, 2010, Bradley et al.

US Office Action dated Dec. 12, 2007 issued in U.S. Appl. No. 10/655,529.

US Office Action Final dated Jul. 3, 2008 issued in U.S. Appl. No. 10/655,529.

US Office Action dated Mar. 17, 2006 issued in U.S. Appl. No. 10/656,898.

US Office Action Final dated Oct. 20, 2006 issued in U.S. Appl. No. 10/656,898.

US Office Action dated May 7, 2007 issued in U.S. Appl. No. 10/656,898.

US Office Action Final dated Jan. 17, 2008 issued in U.S. Appl. No. 10/656,898.

US Office Action dated Jul. 24, 2008 issued in U.S. Appl. No. 10/656,898.

US Office Action dated Jul. 14, 2008 issued in U.S. Appl. No. 11/019,792.

US Notice of Allowance dated Feb. 11, 2009 issued in U.S. Appl. No. 11/019,792.

US Office Action dated Jul. 26, 2010 issued in U.S. Appl. No. 12/485,793.

US Office Action Final dated Feb. 10, 2011 issued in U.S. Appl. No. 12/485,793.

US Office Action dated Apr. 16, 2008 in U.S. Appl. No. 11/488,456.

US Office Action Final dated Jan. 14, 2009 in U.S. Appl. No. 11/488,456.

US Office Action dated Mar. 17, 2009 issued in U.S. Appl. No. 11/588,845.

US Office Action dated Oct. 7, 2010 issued in U.S. Appl. No. 12/560,316.

US Final Office Action dated Jun. 28, 2011 issued in U.S. Appl. No. 12/560,316.

US Office Action dated Oct. 29, 2008 issued in U.S. Appl. No. 11/259,414.

US Final Office Action Apr. 28, 2009 in U.S. Appl. No. 11/259,414.

US Office Action dated Dec. 28, 2009 in U.S. Appl. No. 12/607,912.

US Office Action dated Jun. 1, 2005 issued in U.S. Appl. No. 10/940,324.

US Office Action dated Mar. 3, 2006 issued in U.S. Appl. No. 10/940,324.

US Office Action dated Sep. 7, 2006 issued in U.S. Appl. No. 10/940,324.

US Office Action Final dated Feb. 21, 2007 issued in U.S. Appl. No. 10/940,324.

US Office Action dated Aug. 27, 2007 issued in U.S. Appl. No. 10/940,324.

US Office Action Final dated May 27, 2008 issued in U.S. Appl. No. 10/940,324.

US Office Action dated Aug. 12, 2008 issued in U.S. Appl. No. 10/940,324.

US Office Action dated Apr. 16, 2009 issued in U.S. Appl. No. 10/940,324.

US Office Action dated Apr. 1, 2008 issued in U.S. Appl. No. 11/111,121.

US Notice of Allowance dated Oct. 8, 2008 issued in U.S. Appl. No. 11/111,121.

US Office Action dated Dec. 2, 2005 issued in U.S. Appl. No. 10/945,803.

US Office Action Final dated Apr. 6, 2007 issued in U.S. Appl. No. 10/945,803.

US Office Action Final dated Sep. 12, 2007 issued in U.S. Appl. No. 10/945,803.

US Office Action dated Jun. 12, 2008 issued in U.S. Appl. No. 10/945,803.

US Notice of Allowance dated Jul. 7, 2008 issued in U.S. Appl. No. 10/945,803.

US Office Action Final dated Nov. 2, 2009 issued in U.S. Appl. No. 12/268,327.

US Office Action dated Jun. 1, 2006 issued in U.S. Appl. No. 10/704,066.

US Office Action Final dated Jan. 24, 2007 issued in U.S. Appl. No. 10/704,066.

US Office Action dated Aug. 24, 2007 issued in U.S. Appl. No. 10/704,066.

US Notice of Abandonment and Examiner Interview Summary dated Mar. 6, 2008 issued in U.S. Appl. No. 10/704,066.

US Office Action dated Feb. 25, 2008 issued in U.S. Appl. No. 11/274,747.

US Office Action Final dated Feb. 11, 2009 issued in U.S. Appl. No. 11/274,747.

US Office Action dated Oct. 3, 2008 issued in U.S. Appl. No. 11/400,038.

US Office Action Final dated Jul. 7, 2009 issued in U.S. Appl. No. 11/400,038.

US Office Action dated Feb. 4, 2011 issued in U.S. Appl. No. 11/400,038.

US Notice of Allowance dated Nov. 25, 2011 issued in U.S. Appl. No. 11/400,038.

US Office Action dated Jun. 13, 2013 issued in U.S. Appl. No. 13/442,856.

(56) References Cited

OTHER PUBLICATIONS

US Office Action dated May 12, 2010 issued in U.S. Appl. No. 11/924,328.
US Notice of Allowance dated Dec. 16, 2010 issued in U.S. Appl. No. 11/924,328.
US Notice of Allowance dated Jan. 21, 2011 issued in U.S. Appl. No. 11/924,328.
US Response to Rule 312 Communication dated Feb. 11, 2011 issued in U.S. Appl. No. 11/924,328.
US Notice of Allowance dated Jun. 19, 2013 issued in U.S. Appl. No. 13/084,465.
US Notice of Allowance dated Oct. 8, 2013 issued in U.S. Appl. No. 13/084,465.
PCT International Search Report dated Jun. 11, 2008 issued in PCT/US2006/028079.
PCT International Written Opinion dated Jun. 11, 2008 issued in PCT/US2006/028079.
PCT International Preliminary Report on Patentability and Written Opinion dated Jul. 1, 2008 issued in PCT/US2006/028079.
EP Extended Search Report, Supplementary European Search Report and the European Search Opinion dated Feb. 11, 2011 issued in EP 06 85 1621.
PCT International Search Report dated Oct. 27, 2008 issued in PCT/US2007/008422.
PCT International Written Opinion dated Oct. 27, 2008 issued in PCT/US2007/008422.
PCT International Preliminary Report on Patentability and Written Opinion dated Nov. 27, 2008 issued in PCT/US2007/008422.
EP Extended EP Search Report, Supplementary EP Search Report, and EP Search Opinion dated Nov. 10, 2009 issued in EP 07 75 4869.1.
EP Examination Report dated Mar. 5, 2010 issued in EP 07 75 4869.1.
PCT International Search Report dated Sep. 22, 2005 issued in PCT/US2004/030136.
PCT International Written Opinion dated Sep. 22, 2005 issued in PCT/US2004/030136.
PCT International Preliminary Report on Patentability and Written Opinion dated Jul. 31, 2006 issued in PCT/US2004/030136.
European Search Report dated Mar. 30, 2007 issued in EP 04 788 761.
European Examination Report dated Feb. 10, 2010 issued in EP 04 788 761.7.
Japanese Office Action dated Jul. 13, 2010 issued in JP 2006-526418.
PCT International Search Report dated Nov. 6, 2007 issued in PCT/US2004/030562.
PCT International Preliminary Report on Patentability and Written Opinion dated Nov. 23, 2007 issued in PCT/US2004/030562.
European Supplementary Search Report dated Mar. 9, 2012 issued in EP 04 821 666.7.
European Examination Report dated Oct. 9, 2012 issued in EP 04 821 666.7.
PCT International Search Report dated Mar. 30, 2004 issued in WO 2004/044586.
PCT International Preliminary Examination Report dated Nov. 16, 2006 issued in WO 2004/044586.
European Examination Report dated May 19, 2006 issued in EP03768779.5.
European Examination Report dated Dec. 22, 2009 issued in EP03768779.5.
European Examination Report dated Jul. 13, 2010 issued in EP03768779.5.
Japanese Office Action issued Oct. 8, 2009 issued in JP2005-507121 (as translated by foreign associate in letter dated Nov. 2, 2009), 3pgs.
PCT International Search Report dated Jun. 11, 2008 issued in WO 2008/052104.
PCT International Preliminary Report on Patentability and Written Opinion dated Jun. 11, 2008 issued in WO2008/052104.
PCT International Search Report dated Apr. 29, 2011 issued in PCT/US2010/044778.

PCT International Preliminary Report on Patentability and Written Opinion dated Feb. 16, 2012 issued in PCT/US2010/044778.
European Extended Search Report dated May 24, 2013 issued in EP 10 807 259.6.
Ang, L.M. et al. (Jan. 1, 2000) "Decoration of activated carbon nanotubes with copper and nickel," *Carbon, Elsevier, Oxford, GB*, 38(3):363-372, XP004186284.
Baeumner A.J., et al., (Jan. 1, 2004) "A Universal Nucleic Acid Sequence Biosensor With Nanomolar Detection Limits," *Analytical Chemistry* 20040215, American Chemical Society, 76(4):888-894.
Choi, Hee Cheul et al., (Aug. 1, 2002) "Spontaneous Reduction of Metal Ions on the Sidewalls of Carbon Nanotubes," *Journal of the American Chemical Society*, 124(31):9058-9059, XP55019757.
Collins et al., (Apr. 2, 2001) "Current Saturation and Electrical breakdown in Multiwalled Carbon Nanotubes", *Phys. Rev. Lett.*, 86(14):3128-3131.
Collins et al., (Apr. 27, 2001) "Engineering Carbon Nanotubes and Nanotube Circuits Using Electrical Breakdown", *Science*, 292:706-709.
Cui, Yi et al., (2001) "Nanowire Nanosensors for Highly Sensitive and Selective Detection of Biological and Chemical Species", *Science*, 293:1289-1292.
Dai, H. (2002) "Carbon nanotubes: opportunities and challenges", *Surface Science*, 500:218-241.
Derycke et al., (Sep. 2001) "Carbon Nanotube Inter-and Intramolecular Logic Gates", *Nano Letters*, 1(9):453-456.
Duck et al., (Jan. 1, 1990) "Probe Amplifier System Based on Chimeric Cycling Obigonucleotides," Biotechniques, Natick, MA, 9(2), XP000406092, 9(2):Abtract; figure 1.
Gabriel et al. (2003) "Large Scale Production of Carbon Nanotube Transistors: A Generic Platform for Chemical Sensors", *Mat. Res. Soc. Symp. Proc.*vol. 776:Q12.7.1-Q12.7.7.
Goodrich, Terry, et al, (Apr. 7, 2004) Direct Detection of Genomic DNA by Enzymatically Amplified SPR Imaging Measurements of RNA Microarrays, Journal of the American Chemical Society, 126(13):4086-4087.
Harutyunyan A. R. et al. (May 1, 2002) "Carbon Nanotubes for Medical Applications," *European Cells and Materials, Swiss Society for Biomaterials*, 3(Supplement 2):84-87, XP002365698, ISSN: 1473-2262.
Hu, P. et al., (2008) "Magnetic particle-based sandwich sensor with DNA-modified carbon nanotubes as recognition elements for detection of DNA hybridization", *Analytical Chemistry*, 80(5):1819-1823.
Kietis et al. (2001), "Electrical-to-mechanical coupling in purple membranes: membrane as electrosrictive medium." *Biophysical Jrnl*, vol. 80, pp. 1631-1640.
Kong et al., (Sep. 14, 2001) "Functionalized Carbon Nanotubes for Molecular Hydrogen sensors", *Adv. Mater*, 13(18):1384-1386, XP002504653.
Lee, et al. (Aug. 15, 2005) "Enzymatically Amplified Surface Plasmon Resonance Imaging detection of DNA by Exonuclease III Digestion of DNA Microarrays," *Chemical Society* US, 77(16):5096-5100.
Lin, Yi et al., (Jan. 18, 2002) "Functionalization Multiple-Walled Carbon Nanotubes with Aminopolymers," *Jnl of Phy Chem, B, Materials, Surfaces, Interfaces and Biophysical*, Washington DC U.S. 106(6)1294-1298; XP002971880.
Ng, H.T. et al., (Dec. 2001) "Flexible Carbon Nanotube Membrane Sensory System: A Generic Platform", *Journal of Nanoscience and Nanotechnology*, 1(4):375-379.
Ong et al., (Nov. 2, 2001) "A Carbon Nanotube-based Sensor for $CO_2$ Monitoring ", SENSORS, MDPT, BASEL, SU, 1(6):193-205.
Pearce, Megan E. et al.(Aug. 8, 2007) "Multifunctional Nanorods for Biomedical Applications," *Pharmaceutical Research, Kluwer Academic Publishers-Plenum Publishers*,24(12):2335-2352, XP01955914, ISSN 1573-904X, DOI: 10.1 007/S11 095-007-9380-7.
Perkins et al. (Apr. 16, 2001) "Electrical and materials properties of $ZrO2$ gate dielectrics grown by atomic layer chemical vapor deposition", *Applied Physics Letters*, 78(16):2357-2359.
Qi et al., (2003) "Toward Large Arrays of Multiplex Functionalized Carbon Nanoturbe Sensors for Highly Sensitive and Selective Molecular Detection", *NANO Letters*, 3(3):347-351.

(56) References Cited

OTHER PUBLICATIONS

Radosavljevic et al. (2001) "High-Field electrical transport and breakdown in bundles of single-wall carbon nanotubes", *Phy. Rev. B.* 64, pp. 241307-1 to 241307-4.

Shim et al. (2002) "Functionalization of Carbon Nanotubes for Biocompatibility and Biomolecular Recognition", *Nano Letter*, 2(4):285-288, Published on Web Jan. 25, 2002.

Shim et al., (2001) "Polymer Functionalization for Air-Stable n-Type Carbon Nanotube Field-Effect Transistors", *J Am. Chem Soc.*, 123(46):11512-11513.

Simon, (2001) "Micromachined metal Oxide gas sensors: opportunities to improve sensor performance", *Sensors and Actuators*, 73:1-26.

Skubal et al. (2002) "Detection and identification of gaseous organics using a $TiO_2$ sensor", *Journal of Photochemistry and Photobiology A: Chemistry*, 148:103-108.

Star et al. (Jan. 24, 2006) "Label-free detection of DNA hybridzation using carbon nanotube network field-effect transistors," *Proc. Nat'l. Acad. Sci. USA.*, 103(4):921-926.

Star et al., (Jan. 1, 2003) "Electronic Detection of Specific Protein Binding Using Nanotube", NANO Letters, ACS Washington DC, US, 3(4):459-463 XP002993429.

Suri et al., (2002) "Gas and Humidity Sensors Based on Iron Oxide-Polypyrrole Nanocomposites", *Sensors and Actuators*, B81:277-282.

U.S. Appl. No. 14/306,156, filed Jun. 16, 2014, Bryant et al.

US Office Action dated May 21, 2014 issued in U.S. Appl. No. 12/560,316.

US Final Office Action dated Feb. 5, 2014 issued in U.S. Appl. No. 13/442,856.

Chinese Office Action dated Sep. 3, 2013 issued in CN 201080035150.6.

Wilson L. J. (Dec. 1, 2005) "New carbon nanostructures for imaging and therapy of breast cancer," *Breast Cancer Research and Treatment, Kluwer Academic Publishers*, BO, 94(1):S1-S301,, MS1-1, XP019274939, ISSN:1573-7217.

US Notice of Allowance dated Jan. 27, 2014 issued in U.S. Appl. No. 13/084,465.

Stetter et al., (Feb. 23, 2003) "Nano-Electronic Sensors; Practical Device Designs for Sensors", *Nanotechnology Conference and Trade Show, Nanotech, Joint Meeting, International Conference on Modeling and Simulation of Microsystems, MSM, International Conference on Computational Nanoscience and Technology*, 3(23):313-316.

\* cited by examiner

MAGNETIC CARBON NANOTUBE BASED BIODETECTION

CROSS-REFERENCE TO RELATED APPLICATION

This application claims benefit pursuant to 35 USC. §119(e) of U.S. Provisional Patent Application No. 61/232,242 filed Aug. 7, 2009. This application is incorporated by reference herein.

BACKGROUND

Electrochemical immunosensors based on single-wall CNT forest platforms with multi-label secondary antibody nanotube bioconjugates have been reported as highly sensitive detection platform. (Xin et al. "Carbon Nanotube Amplification Strategies for Highly Sensitive Immunodetection of Cancer Biomarkers", Journal of the American Chemical Society 2006 128 (34), pp 11199-11205, incorporated by reference herein). In this case, the SWNT forest was standing in upright bundles on Nafion-iron oxide decorate conductive surface. Amplified sensitivity was achieved by using bioconjugates featuring horseradish peroxidase (HRP) labels and secondary antibodies (Ab2) linked to multiwall CNT at high HRP-to-Ab2 ratio to replace singly labeled secondary antibodies. Due to the complexity of fabrication process for the CNT forest, an alternative platform using densely packed AuNPs was recently reported. (Vigneshwaran Mani et al. "Ultrasensitive Immunosensor for Cancer Biomarker Proteins Using Gold Nanoparticle Film Electrodes and Multienzyme-Particle Amplification", ACS Nano Letters, 2009, 3 (3), pp 585-594, incorporated by reference herein). In the study, HRP labels were attached to carboxyl groups created on the magnetic bead surface to improve the sensitivity and detection limit. After the bioconjugation of HRP and Ab2, the free antibodies and HRP were easily separated from the Ab2 magnetic bead-HRP by using a magnet to localize the beads at the bottom of a test tube and washing to remove unreacted protein. Magnetic particles for medical applications have been developed. Since magnetic particles have unique magnetic features not present in other materials, they can be applied to special medical techniques. See, e.g., Choi, J-W et al. "An integrated microfluidic biochemical detection system with magnetic bead-based sampling and analysis capabilities." Electrochemistry Communications. 2001, 9, pp 1547-1552. and R. E. Thilwind, et al. "Measurement of the concentration of magnetic nanoparticles in a fluid using a giant magnetoresistance sensor with a trench." J. Magnetism and Magnetic Materials, 2008, 320, pp 486-489, both incorporated by reference herein.

Separation, immunoassay, magnetic resonance imaging (MRI), drug delivery, and hyperthermia are enhanced by the use of magnetic particles. An example of magnetic particles used in biodetection to enable point-of-care diagnostics was recently demonstrated by Philips' Magnotech handheld technology. Integrated into a disposable biosensor cartridge that inserts into a hand-held analyzer, Magnotech uses magnetic nanoparticles to measure target molecules in picomolar concentrations in just a few minutes. Furthermore, the technology improves ease of use by simplifying fluidic washing steps. Although magnetic beads have been used in various biodetection applications, they often involve complex surface functionalization. The conformity and stability of the surface coating can affect toxicity and robustness of bindings.

SUMMARY

Provided herein is a new hybrid material system, mCNT, including magnetic carbon nanotubes for biological and medical sensing applications. In certain embodiments, the systems include magnetic material on the interior of carbon nanotubes (CNTs). The amount of magnetic particles inside CNTs may be such that mCNT can respond to small, low cost, portable magnet. The exterior CNT surface is kept intact for biomolecular attachments or other functionalizations. Performance enhancement with this novel material includes improved sensitivity, reduced response time, and reduced sample volume. According to various embodiments, the mCNTs are substrates for the adherence of molecules participating in these assays or as active sensing elements. Also provided are methods of fabricating two-dimensional mCNT and CNT networks on printed electrodes.

One aspect of the invention relates to a mCNT material including a carbon nanotube having an interior cavity and an exterior surface; a magnetic material disposed within the interior cavity; and a plurality of capture agents attached to the exterior surface. The capture agent may be any molecule that can bind to or otherwise capture a target. The capture agents may be organic or non-organic capture agents, including synthetic and non-synthetic agents. Examples of biomolecular capture agents include antibodies, enzymes, oilgonucleotides, aptamers, antibody fragments, and molecularly imprinted polymers. In certain embodiments, the capture agents attached to the nanotubes may be reporter agents, such as antibodies, configured to selectively or non-selectively bind to a target. In many embodiments, the magnetic material is a ferromagnetic material, such iron, cobalt, nickel, or alloys or mixtures thereof, in the form of particles, e.g., nanoclusters. According to various embodiments, the mCNT material includes a plurality of such carbon nanotubes. In certain embodiments, the mCNT is provided out-of-solution, e.g., in the form of a powder or tablet. In other embodiments, the mCNT material is in solution. The plurality of carbon nanotubes in solution form a mesh network under application of a magnetic field in certain embodiments. In certain embodiments, the magnetic material is confined to the interior cavity of the nanotube(s), such that there is essentially none of the magnetic material on the exterior surface of the nanotubes, or otherwise outside of the nanotube interior cavity. The cavity ends may be open or closed.

Another aspect of the invention relates to a method of sensing a biomolecular target in a sample. In certain embodiments, the method includes providing a plurality of carbon nanotubes having an interior cavity and an exterior surface with a magnetic material disposed within the interior cavity; and a plurality of capture agents configured to bind to the target attached to the exterior surface; dispersing the plurality of carbon nanotubes into a solution; contacting the plurality of carbon nanotubes with the sample to bind biomolecular targets in the sample to capture agents in solution; applying a magnetic field to bring the plurality of carbon nanotubes in the solution toward a sensing electrode; and sensing the presence of the target.

Another aspect of the invention relates to a system for sensing a biomolecular target in a solution including a sample container; an electrode configured to contact a sample within the sample container; a plurality of carbon nanotubes having an interior cavity and an exterior surface with a magnetic material disposed within the interior cavity; and a plurality of capture agents configured to bind to the target attached to the exterior surface; and a magnet configured to exert a magnetic force to the plurality of carbon nanotubes to move with respect to the electrode.

These and other aspects of the invention are discussed further below with reference to the drawings.

DETAILED DESCRIPTION

The present invention provides a new material system that enables independent control of the surface characteristics and magnetic property. According to various embodiments, the present invention relates to high performance chemical and biological detection using carbon nanotubes (CNTs). In certain embodiments, a new hybrid material system, with nanomagnetic material embedded within the CNTs for detection of biological and other targets is provided. We refer to this hybrid material as mCNTs. This novel material provides enhanced sensing performance in many areas, including improved sensitivity, reduced response time and reduced sample volume. Moreover, this novel material and the concept described herein can be applied in various product configurations. Examples are described below.

In certain embodiments, the mCNTs are used for immunological or other biological assays. The mCNT serves as a substrate for the adherence of multiple molecules participating in these assays. This material will significantly enhance the functional surface area thus enhancing the positive attributes created by magnetic beads and particles. The mCNTs can be used for all target types (nucleic acids, protein, antibody, glycan) and detection platforms (e.g., optical, amperometric, electrochemical, label free) using biological capture.

In certain embodiments, the mCNTs include nanotubes filled with one or more ferromagnetic materials, such as iron, cobalt, nickel, gadolinium, dysprosium, or other material with ferromagnetic properties. Various techniques for encapsulating metals, the introduction of metals or metal carbide and oxide in CNTs may significantly alter their electronic and mechanical properties. For example, it has been shown that the electrical conductance of an individual carbon nanotube is sensitive to magnetic transitions of nanoscale magnets embedded inside it. Nanotubes filled with ferromagnetic materials have also gained considerable interest due to their potential applications in magnetic data storage technology.

In certain embodiments, the mCNTs include nanotube shells with essentially no magnetic material on the exterior surface of the nanotubes. The nanotube shells protect the inner ferromagnetic clusters against oxidation and enhance their long-term stability. In certain embodiments, the mCNT fabrication process includes opening nanotube ends. For example, in certain embodiments CNT purification and acid treatment (e.g., concentrated nitric acid and sulfuric acid oxidation) creates functional groups such as carboxylic acid (—COOH) at the nanotube ends. This is useful for the deposition of metal (ferromagnetic) particles inside the nanotube by the electrochemical method of the reduction of the corresponding metal salt. In certain embodiments, after magnetization of the CNTs, post-processing is applied to cover the ends to avoid exposure of metal particles to ambient and further enhance the stability.

A manufacturing approach to create CNTs with magnetic clusters embedded on the interior of the CNTs has been demonstrated by Soldano et al. ("Detection of nanoscale magnetic activity using a single carbon nanotube", Nano Letters. 2008; 8 (12), pp 4498-4505, incorporated by reference herein.) In their study, the material was used to investigate nanoscale magnetic activity using a single carbon nanotube.

According to various embodiments, the materials are used during biological and medical applications, e.g., in lieu of magnetic beads. The materials have the magnetic material on the interior of the CNTs. If the magnetic material were on the exterior of the CNTs the material would contribute to the electrochemical signal measured during target detection, and in some case, it would increase toxicity. Since the magnetic clusters are located only inside the CNTs, the CNT surface remains intact and can be easily functionalized with chemistry that affords specificity to the target of interest. For example, biomolecular capture agents includes antibodies, enzymes, oilgonucleotides, aptamers, and antibody fragments. Non-biomolecular capture agents may include molecularly imprinted polymers.

Figure 1:
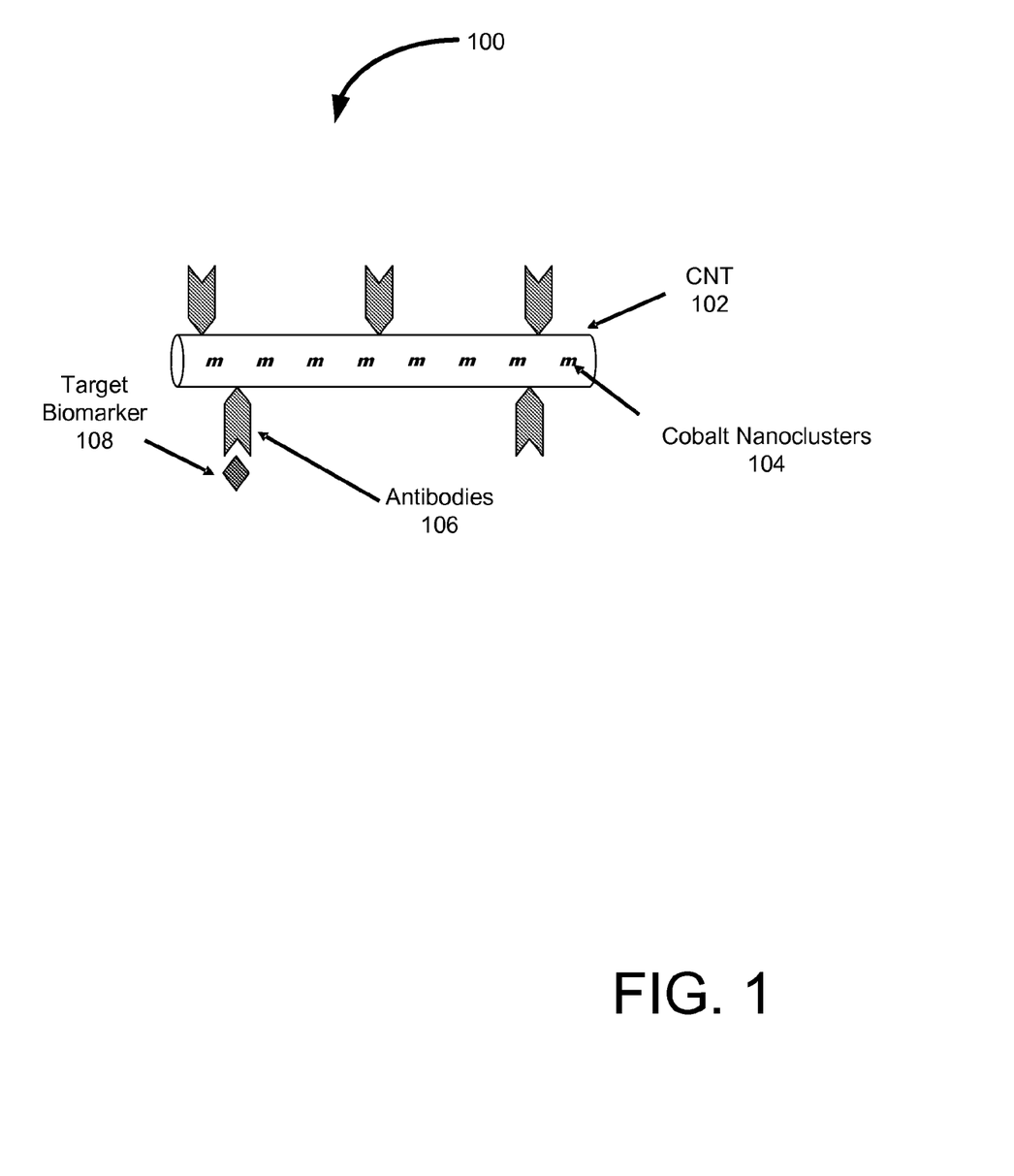
FIG. 1 is a schematic of a mCNT according to certain embodiments, including a carbon nanotube having ferromagnetic particles disposed therein.

FIG. 1 is a schematic of a mCNT 100 according to certain embodiments. mCNT 100 include carbon nanotube 102 having cobalt nanoclusters 104 disposed within. According to various embodiments, diameter of the mCNT can range from about 1 nm to 20 nm with length about 50 nm to millimeters, depending on the application, though the mCNTs are not limited to these specific dimensions. In the example shown in the figure, mCNT 100 includes antibody functionalization on its exterior surface, with antibodies 106 attached to the sidewalls of CNT 102. Antibodies 106 functionalize mCNT 100 to capture target antigen 108. Examples of the capture chemistry that are applied to the mCNTs according to various embodiments are enzymes, nucleic acids, antibodies, aptamers, oligosaccharides, antigens and glycans. Attachment methods include adsorption, covalent bonding, streptavidin/biotin, and any other known method of functionalizing CNTs.

An example of functionalizing and using mCNTs is described below:

1. Biomolecules are attached to mCNTs using physical adsorption or selected chemistry such as carbodiimide or glutaraldehyde cross linking For example, in an electrochemical enzyme-linked immunosorbent assay (ELISA), a capture antibody such as cardiac troponin I may be attached. A target-specific enzyme is attached for a enzymatic assay such as glucose or creatinine detection. One of skill in the art will appreciate that any known capture chemistry may be employed.
2. The un-functionalized surfaces of the mCNTs are blocked by proteins such as bovine serum albumin (BSA) or surfactants such as tween-20 to prevent non-specific sticking of sample or reporter material. The hydrophobic interaction between mCNTs and protein/antibody/surfactants is useful for this.
3. The functionalized mCNTs are put into a solution. The solution can be any of the common liquid for CNT dispersion, for example water, ethanol, dimethylformamide (DMF), tetrahydrofuran (THF), or surfactants such as sodium dodecyl sulfate (SDS) in water. For compatibility with biomolecules aqueous based solvents are preferred The solution of dispersion liquid and mCNT could also contain the reporter chemistry involved in the electrochemical reaction. In some cases a reporter may not be required, which is typically called "label-free." During typical electrochemical ELISA a label is required for signal amplification. A label can be an enzyme such as horseradish peroxidase (HRP) attached to a secondary antibody for the target (i.e., a reporter).

4. The solution is mixed with the sample. Examples of samples are biological samples such as urine, sputum, saliva, blood, exhaled breath condensate, etc. This can be accomplished in a variety of settings. This can be in a tube, micro well plate or preferably in a cartridge that fits into a hand held reader.

Figure 2:
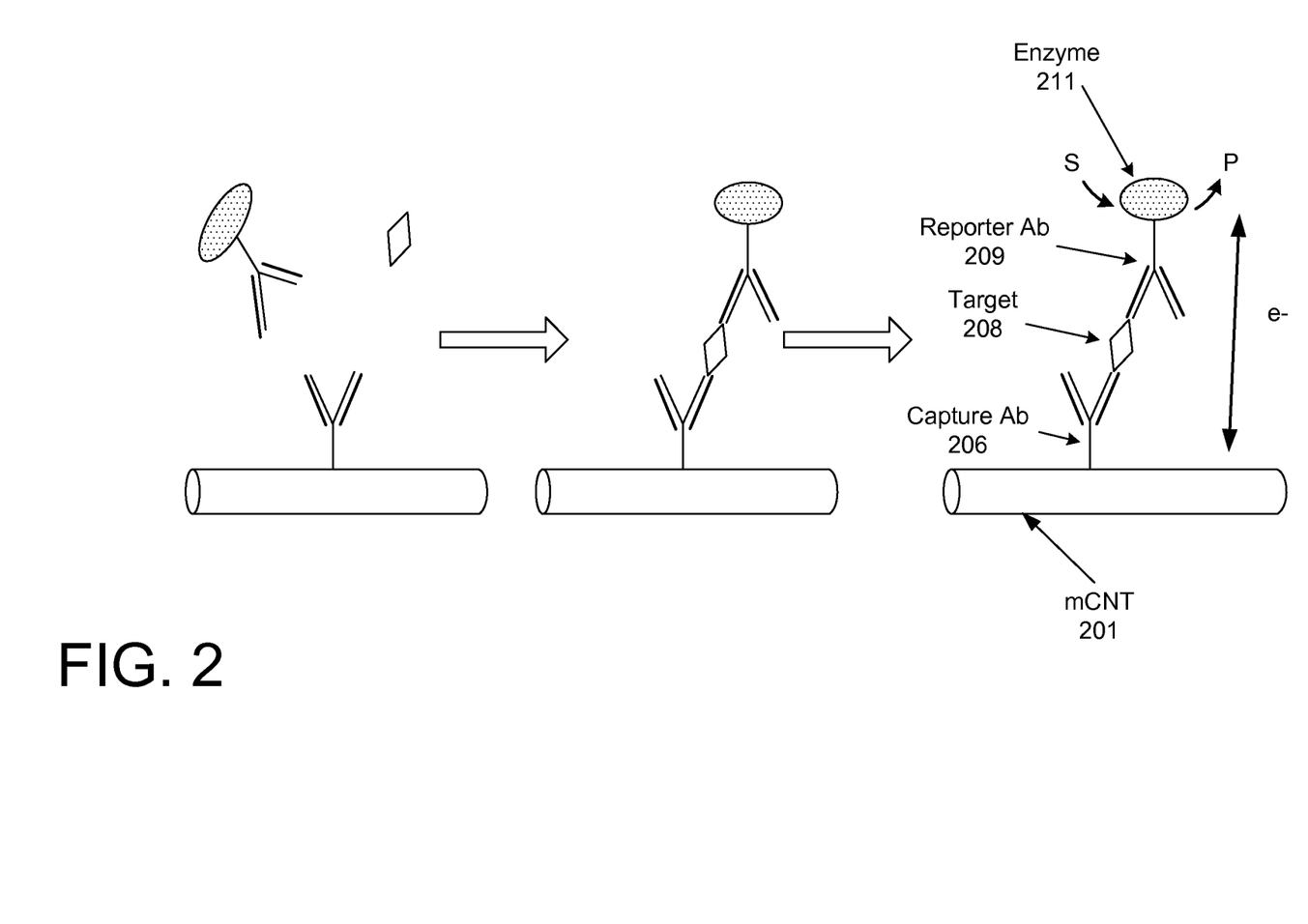
FIG. 2 shows a representative schematic diagram of an assay employing an mCNT according to certain embodiments.

FIG. 2 shows a representative schematic diagram of an assay employing an mCNT according to certain embodiments. Capture antibodies 206 are attached to an mCNT 201, which are held in proximity to a screen printed electrode by magnetic force (not shown). The capture antibodies 206 are configured to capture target 208, which also bind to reporter antibodies 209. Enzyme 211 is attached to reporter antibodies 209 for reporting.

Without mCNTs, an electron shuttle to transfer electrons between the enzyme active site 211 and the electrode 201 is needed due to the fact that the label is located at a distance from the electrode due to the capture antibody, target and secondary antibody (reporter) sandwich. With the use of mCNTs, in certain embodiments, the sandwich formation takes place in the solution. After the application of the magnetic field the entire sandwich assembly including the reporter is physically brought in close proximity to the electrode. This increases the possibility of direct electronic communication between the label and the electrode. As such, the need for the substrate for the detection of the label is obviated. Fewer reagents need to be stored on the product cartridge. It leads to fewer assay steps, thus improving assay speed. It also greatly simplifies the fluidics, valve and pumping requirements. The same principle is also applied to enzymatic assays where direct electronic communication between the enzyme and electrode is established using mCNTs, thereby obviating the need for an electron shuttle.

If the active site of the enzyme or other label is not accessible with CNTs or another compound (a mediator) catalyzes certain reactions faster or with less energy a mediator can be deployed to communicate with the active site. Typical mediators (example 2,2'-azinobis(3-ethylbenzothiazoline-6-sulfonate) (ABTS)$^{ref}$ 1 or 3,3',5,5'-tetramethylbenzidine (TMBB) adsorb on CNTs and are useful for this purpose. The label free approach can be applied selectively to assays with high concentration requirement (e.g. C-reactive protein (CRP)—ng/ml to μg/ml range) from a menu of assays available on the cartridge. In addition to enzymes, other labels that show electrochemical activity such as cytochrome-C (Fe(III) (Cyt c)→Fe (II) (Cyt-c)), colloidal metal crystals such as ZnS, CdS, PbS, CuS can be used and are compatible with the above approach.

The fact that the active elements in the solution contain magnetic components means that magnetic stirring can be employed to enhance the diffusion/encounter rate of the targets and captures. The sandwich formation between the reporter and capture antibodies takes place in the bulk phase that makes the assay faster. This compares with the 2-phase reaction that typically takes place in electrochemical ELISA where the capture antibody is immobilized on the electrodes. Any one of many different motions could be used for the stirring, for example, rotational, lateral, back-and-forth, etc. The degree of total agitation can also be controlled for any number of reasons, for example to prevent formation of emulsions or degrade the mCNT functionalization (low agitation).

In a product configuration involving sample delivery and flow path, a magnet can be used to move the mCNT/capture/target/reporter complexes towards the sensing area. As an example, an electromagnet situated under the cartridges can brings the mCNTs, including the captured target molecules, into contact with the active detection surface of the biosensor. The measurement can be done using optical technique. The measurement can also be done electrically by bringing mCNTs into contact with base electrode that is connected with external circuits.

The mCNTs also have multiple routes for facile attachment of molecules. In contrast, many beads and particles used for multi-enzyme labeling approach have the presence of a single chemical moiety for conjugation, for example, amine or carboxyl groups. The lack of two or more different types of functional groups means there is no facile route for attachment of different types of molecules. For these materials of uniform chemical structure, appropriate kinetic control (i.e. reaction timing) or using appropriate molar ratios of the multiple conjugates is required to obtain a particular loading of each molecule onto the support. In contrast, a single carbon nanotube may have multiple chemical moieties for attachment of different molecules. More specifically, the ends of the carbon nanotubes have a different chemical configuration than the middle portion of the nanotube. In certain embodiments, the sidewall of a CNT is characterized by a sp2 bonding configuration, while the tube ends have dangling bonds making it more reactive than the sidewall. The elevated reactivity may extend toward the center of the tube because of defects. However, this is in the range of a few atoms from the end. Due to the presence of dangling bonds at the end, functional groups may also be created during the purification and functionalization of CNTs, e.g., by acid treatment. This means that the ends of the carbon nanotubes, which are more reactive, can be preferentially converted into one functional moiety while a second, different, chemical moiety is imbued throughout the middle of the nanotube. Alternatively, the ends can be functionalized and the body left unfunctionalized and used for simple physiosorption attachment of molecules. The presence of two separate attachment routes provides for facile construction of these materials, including increased control of the amount of each molecule type on the material.

Figure 3:
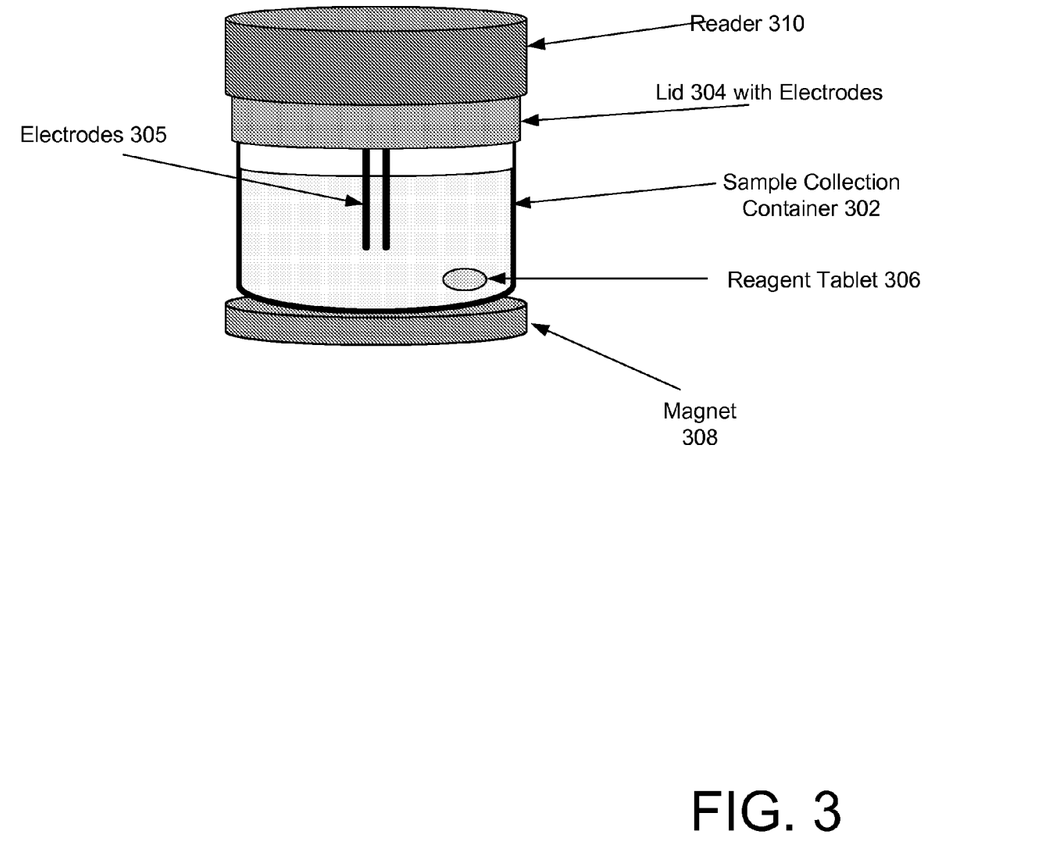
FIG. 3 illustrates an embodiment of a novel diagnostic biosensor for a condition, e.g., active tuberculosis (TB), according to certain embodiments.

In certain embodiments, in addition to replacement of magnetic particles, mCNTs can be used as active sensing elements. In one of the embodiment, mCNTs are deposited on a substrate to form electrodes. The structure and diameters can be independently optimized to achieve the desired electrical characteristics. In additions to the improved chemistry and magnet design discussed above, the high aspect ratio of mCNT allows formation of network structures that can be electrically connected for direct readout. FIG. 3 illustrates an embodiment of a novel diagnostic biosensor for a condition, e.g., active tuberculosis (TB), according to certain embodiments. This biosensor includes aspects of the invention, and is configured to have minimal fluid handling and high sensitivity. It includes a sample container 302, a lid 304 including electrodes 305 attached to the underside of lid 304 to extend into a sample contained in container 302, a magnet 308 that is movable and/or switchable with respect to the container 302, and a reader 310. Magnet 308 may be a permanent magnet that is movable with respect to the container, or an electromagnet that may be turned on or off. A reagent tablet 306 may be placed in the sample container 302 to disperse necessary reagents. As discussed below, these may include mCNTs.

An example of testing protocol using such devices is described below:
1. Collect sample in container
2. Attach Lid
3. Swirl contents (target binds mCNTs)
4. Apply magnetic field (sandwich formation)
5. Reverse magnetic field & swirl (unbound mCNTs stick to bottom of container)
6. Measure capacitance In one embodiment, capture antibodies are immobilized on a standard conductive carbon-ink electrode (i.e., a glucose test strip) that is configured to measure capacitance. The reporter antibodies are immobilized on mCNTs. The magnetic properties are conferred by cobalt nanoclusters electrochemically deposited in the core of the tube. The reporter antibodies bind to the target in the bulk solution; gentle swirling of the solution improves kinetics. Subsequently, a magnet is placed to quickly move the complex to the electrode surface to complete the sandwich formation. Because the antibodies are specific to the target, the presence of the target is necessary for the formation of the sandwich structure. After sandwich formation, the magnet position and/or orientation is changed so that any unbound reporter antibodies are removed from the vicinity of the capacitance electrode, thus conferring target specificity. Any remaining mCNTs (bound via the target) will increase the electrode capacitance, thus indicating the presence of target. The CNTs increase the capacitance of the electrode because they essentially form an electrochemical capacitor (e.g., a porous mesh structure within an electrolyte, the urine). This kind of mesh structure cannot be formed by magnetic beads or other nanoparticles commonly used in other tests, however the high-aspect ratio geometry of the CNTs enables this inventive approach. CNTs have high surface area due to their nanoscale dimensions. This enhances the sensitivity of detection. Any functional groups present on the CNTs (e.g., —COOH) further increases the capacitance change associated with the binding of CNTs to the electrode.

A typical urine sample contains nearly three orders of magnitude more volume than that used by enzyme immunoassay (EIA) and immunochromatic lateral flow (ICLF) tests. This unconventional test is designed to use the entire sample volume available and then use an efficient method to capture the target in the bulk solution and concentrate it at the transducer surface. The test has broad application for the detection of low-abundance molecules in biological or environmental samples that can be collected in or diluted to moderate volume (e.g. urine, drinking water, etc). The proposed test is a combination of components used within several well accepted chemical detection methods. The novel test uses the same antibody sandwich technique (reporter+target+capture) used in EIA and ICLF for target recognition. However, instead of optical reporting of the target, direct electronic measurement is used to further simplify the test.

In certain embodiments, the entire test is performed in a standard urine sample collection container and only requires swirling and moving a permanent magnet. Alternatively, an electromagnet could be used for a no-step assay. Inside the jar is a small water/urine dissolvable capsule containing dry powder of mCNTs already conjugated with the reporter antibody. The sample rehydrates the system so liquid reagents are not required. Significantly, the magnetic separation eliminates any "wash" step since once the unbound mCNTS are micrometers away from the electrode they cease to impact the local capacitance. Thus, the test does not require additional liquid reagents or fluid handling.

In the configuration presented in FIG. 3, the electrodes 305 are attached to the container lid 304 underside and measured by a simple reusable reader 310 resembling a cheap solar powered watch that attaches to the lid topside. The reader provides a digital output of the results. Because the measurement is electronic, positive and negative controls or multiplexed detection of several targets can be done easily.

The biosensor described herein is one of the many examples how mCNTs can be used as target capture and sensing elements. In addition to the wide variety of the wide variety of antigen and antibody detection with immunological elements, the various assay types that may employ mCNTs according to embodiments of the invention include:

1) capture specific and detect specific cells out of solution, e.g. CD4 (See, e.g., Gao et al., Magnetic based immunoassay for enumeration of CD4(+) T lymphocytes on a microfludic device. Talanta 82:528-533 (2010), incorporated by reference herein) or cancer (See, e.g., Ma et al., Magnetization of large polystyrene peptide beads for capturing and expanding cancer cells. J. of Magnetisim and Magnetic Materials 264: 153-157 (2003), incorporated by reference herein.)

2) nucleic acid hybridization assays (See, e.g., Shepard, A. R and J. L. Rae., Magnetic capture of cDNAs from double-stranded plasmid cDNA libraries. Nucleic Acids Research 25:3183-3185 (1997), incorporated by reference herein.)

3) integration with sample to answer nucleic acid amplification systems (See e.g., Dill et al. Fully integrated device for direct sample-to-answer genetic analysis. Integrated Analytical Systems: Microarrays, Springer New York (2009), incorporated by reference herein.)

4) flow cytommetry (See e.g.m Yang et al, Biosensors and Bioelectronics 24:855-862 (2008), incorporated by reference herein.)

5) agglutination assays (e.g. Moser et al.m On-chip immuno-agglutination assay with analyte capture by dynamic manipulation of superparmagnetic beads. Lab on a Chip 9:3261-3267 (2009), incorporated by reference herein); and 6) lipid analysis (e.g. Nauck et al., New immunoseparation-based homogeneous assay for HDL-cholesterol compared with three homogeneous and two heterogeneous methods for HDL-cholesterol., Clinical Chemistry 44:1443-1451 (1998), incorporated by reference herein.)

One of skill in the art will understand based on the teachings described herein how to apply the mCNTs in place of magnetic beads and other magnetic elements in these assays, as well as in the wide variety of the wide variety of antigen and antibody detection with immunological elements.

Figure 4:
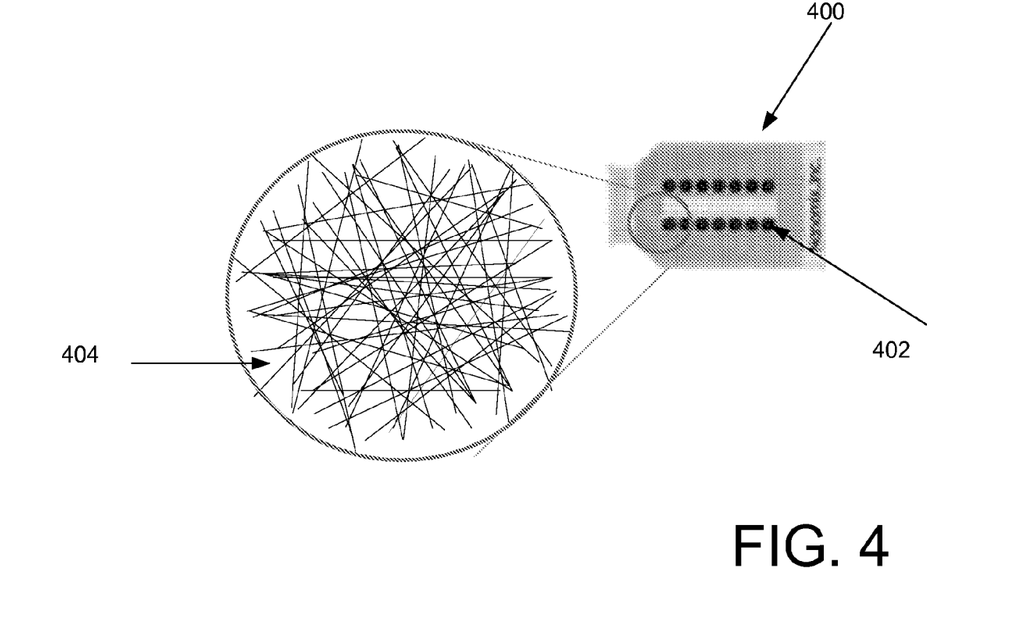
FIG. 4 shows an image of a device 400 having electrodes 402 including CNTs 404.
Figure 5:
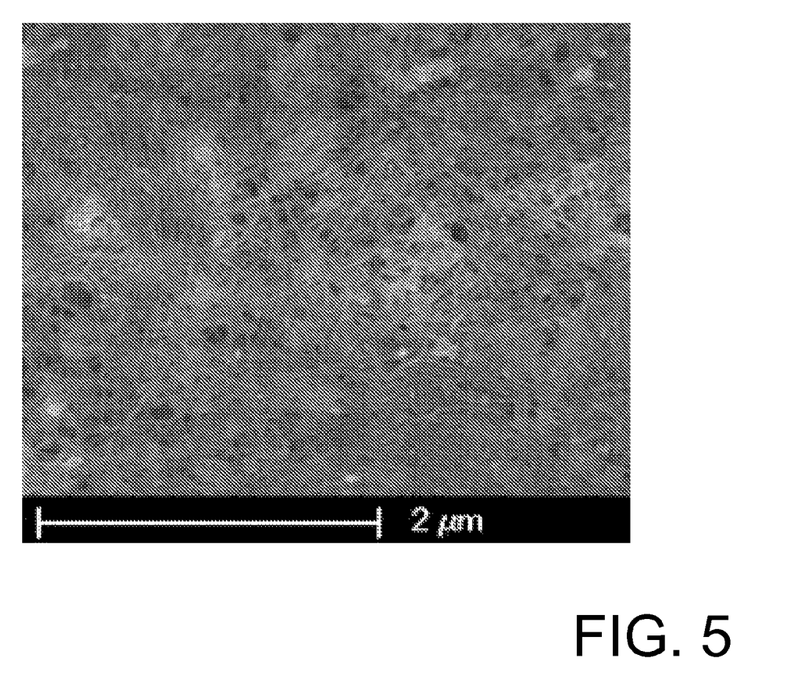
FIG. 5 is an SEM image of a randomly distributed CNT network on a screen printed base electrode.

Another aspect of the invention relates to a CNT network combined with CNT based amplification scheme. The combination of electrochemical immunosensors based on single-wall CNT forest platforms with multi-label secondary antibody nanotube bioconjugates has been previously demonstrated. A SWNT forest was standing in upright bundles on Nafion-iron oxide decorate conductive surface. Improved sensitivity was achieved. However, the realization of the technology is hampered due to the complexity of the electrode fabrication process. In certain embodiments, CNT and/or mCNT networks are used as electrodes. The base electrode can be produced by common means such as screen printing. A CNT and/or mCNT network can be deposited on the base electrode using commercially available equipment, e.g., a Biodot. FIG. 4 shows an image of a device 400 having electrodes 402 including CNTs 404. An example of an SEM (scanning electron microscope) picture of the CNTs deposited by a Biodot on a finished device is shown in FIG. 5.

Results indicate uniform distribution of the carbon nanotube network on electrodes defined by screen printed carbon ink.

Various methods are employed for the electrochemical detection. For multiplexing different enzyme labels, metal nano particles, and/or other electro active labels are used. With an enzyme label attached to the reporter antibody, redox current for the mediator in the presence of the enzyme substrate is used to quantify the target by amperometry. Multiple enzyme labels can be attached to the CNTs along with the reporter antibodies to get more enzyme molecules per binding event. Other labels that show electrochemical activity such as cytochrome-C(Fe(III)(Cyt c)→Fe (II) (Cyt-c)) may be used to reduce the number of steps. The CNTs or reporter antibodies may also be labeled by colloidal metal crystals such as ZnS, CdS, PbS, and/or CuS and detected by anodic stripping voltammetry.

EXAMPLE

Figure 6:
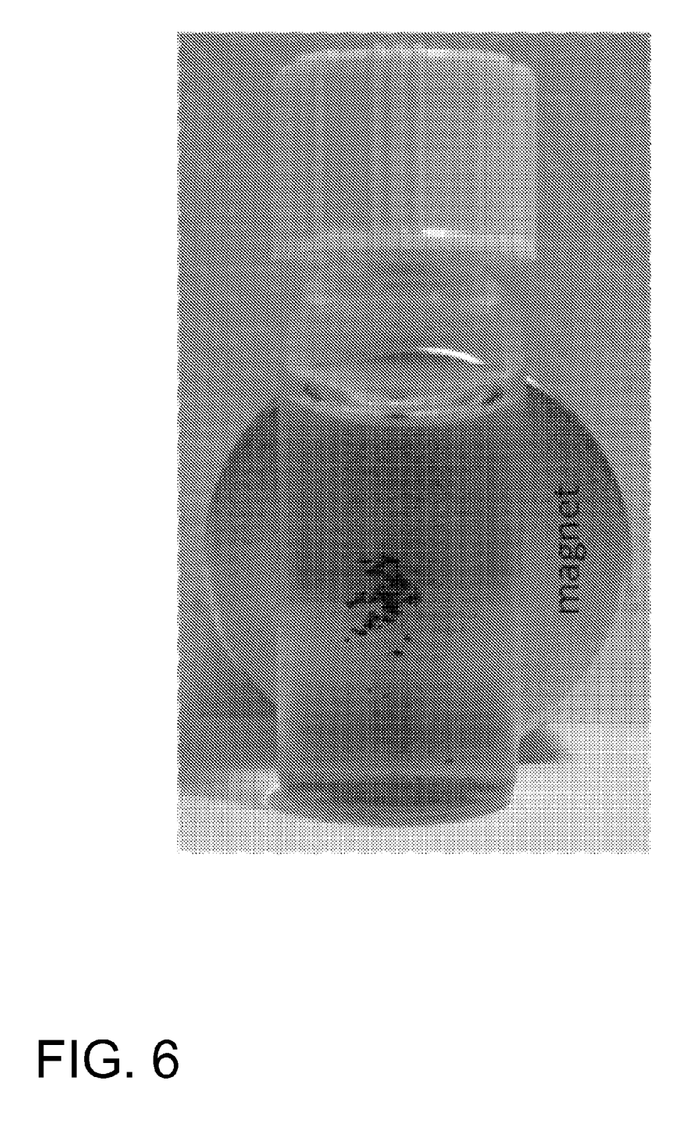
FIG. 6 is an image of mCNTs suspended in solution under application of a magnetic field.

CNTs were grown in an Anodized Alumina template by chemical vapor deposition (CVD). CNT diameter was easily controlled by the template pore size. Electrochemical deposition was then employed to form ferromagnetic nanoparticles inside the nanotubes (mCNTs). The ensemble behavior of thousands of embedded magnetic nanoparticles and their ability to confer strong paramagnetic behavior to CNTs was investigated. Results indicate that the mCNTs indicate that the embedded magnetic nanoclusters are sufficient to provide excellent separation characteristics. FIG. 6 is an image of the mCNTs separated out of the bulk solution using a permanent magnet. The mCNTs are in ultra pure water, separated out of solution using a permanent magnet (labeled) placed behind the glass vial. In contrast, non magnetic CNTs would settle to the bottom of the vial.

Having thus described preferred embodiments of the methods and devices having aspects of the invention, it should be apparent to those skilled in the art that there are certain advantages to this system. It should also be appreciated that various modifications, adaptations, and alternative embodiments thereof may be made within the scope and spirit of the present invention. Different labels and electrochemical measurement methods can be applied to magnetic CNTs based system, this will be obvious to those skilled in the art. Thus the performance measures such as sensitivity and specificity of the device can be balanced with the need for additional fluid handling and measurement steps as necessary for the particular application.

The invention claimed is:

1. A mCNT material comprising:
a carbon nanotube having an interior cavity and an exterior surface;
a magnetic material disposed within the interior cavity; and
a plurality of chemical moieties, wherein a first species of chemical moiety is attached to the exterior surface of the nanotube at the ends of the nanotube and a second species of chemical moiety is attached to the exterior surface of the nanotube at the middle of the nanotube.

2. The mCNT material of claim 1 wherein the magnetic material is selected from at least one of cobalt, iron and nickel.

3. The mCNT material of claim 1 wherein the mCNT material is in the form of a powder.

4. The mCNT material of claim 1, further comprising a plurality of the mCNTs of claim 1 in a solution, wherein the plurality of mCNTs are configured to form a mesh within the solution under application of a magnetic field.

5. The mCNT material of claim 1 wherein there is essentially no magnetic material on the exterior surface.

6. The mCNT material of claim 1 wherein one or more cavity ends are opened.

7. The mCNT material of claim 1, wherein the first species of chemical moiety is a first species of capture agent, and the second species of chemical moiety is a second species of capture agent.

* * * * *